United States Patent [19]

Tuchband et al.

[11] 4,221,295
[45] Sep. 9, 1980

[54] MID-STREAM URINE COLLECTION DEVICE AND PACKAGE THEREFOR

[76] Inventors: Steve Tuchband, 91 Bunker Hill Dr., Trumbull, Conn. 06611; John Uhoch, Jr., 313 Beach Ave., Warwick, R.I. 02889

[21] Appl. No.: 3,098
[22] Filed: Jan. 12, 1979
[51] Int. Cl.³ .................. B65D 69/00; B65D 71/00
[52] U.S. Cl. .................. 206/569; 206/570; 206/564
[58] Field of Search ............. 206/569, 570, 223, 564, 206/523, 592; 128/760, 295, 272; 4/110, 144.1, 144.3

[56] References Cited

U.S. PATENT DOCUMENTS

| | | | |
|---|---|---|---|
| 3,420,361 | 1/1969 | Newberg | 206/223 |
| 3,811,136 | 5/1974 | Whitney et al. | 128/760 |
| 3,832,738 | 9/1974 | Kliemann | 128/295 X |
| 3,881,465 | 5/1975 | Raitto | 4/144.1 |
| 3,987,895 | 10/1976 | Jamshidi | 206/570 |
| 4,064,760 | 12/1977 | Benjamin | 128/760 |

FOREIGN PATENT DOCUMENTS 2603434  8/1977  Fed. Rep. of Germany .......... 206/523

Primary Examiner—Joseph Man-Fu Moy
Attorney, Agent, or Firm—Morgan, Finnegan, Pine, Foley & Lee

[57] ABSTRACT

A package and device for collecting urine wherein the parts comprising the device are packaged so that they are removed in the order that they are used and are maintained in a sterile condition prior to use.

The device includes instructions, cleansing means, a container, funnel assembly, a cap for the container and an identification label packaged in such a manner so as to be sterile before use and removed aseptically in the order that such parts are used.

1 Claim, 8 Drawing Figures

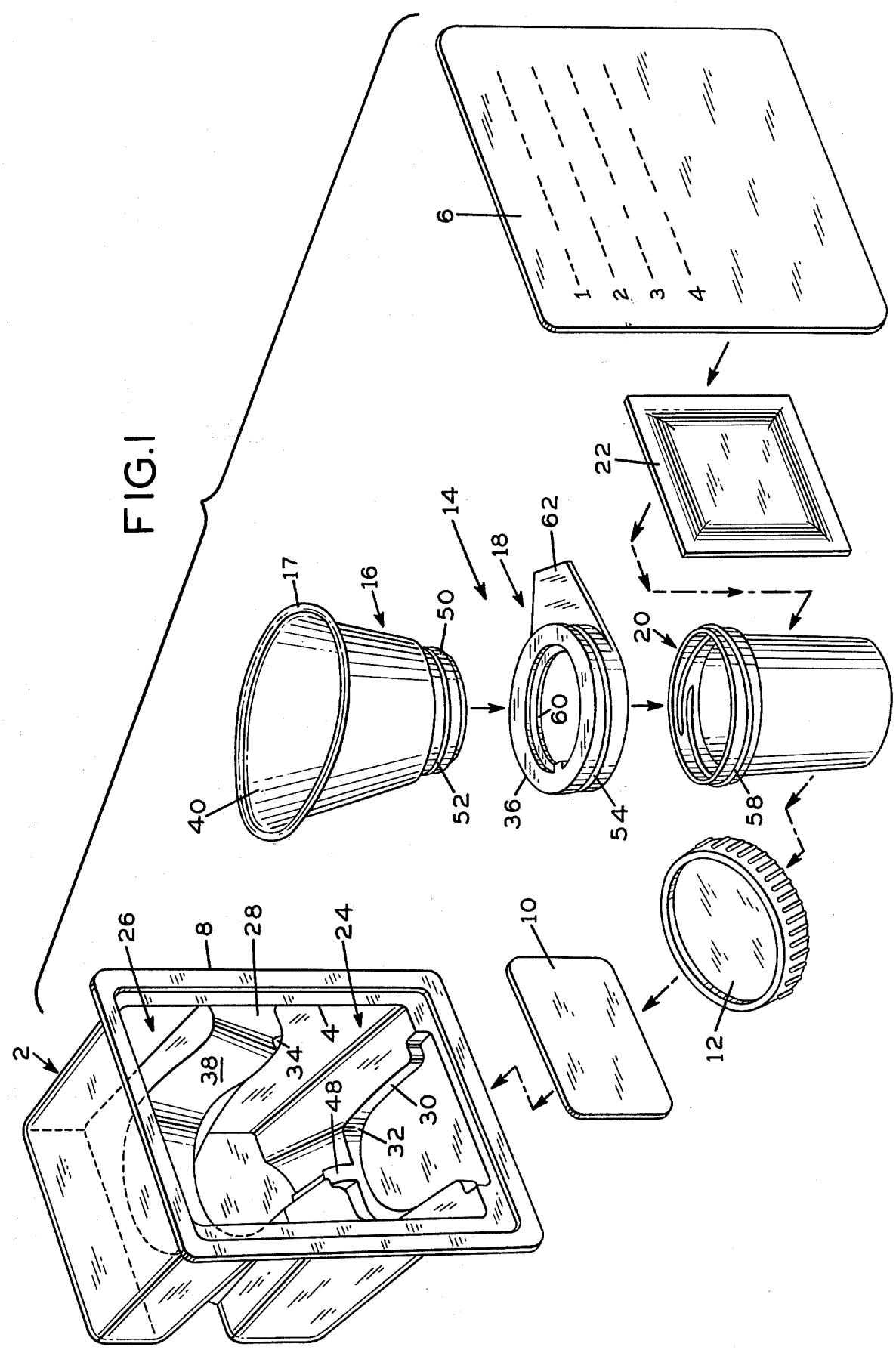

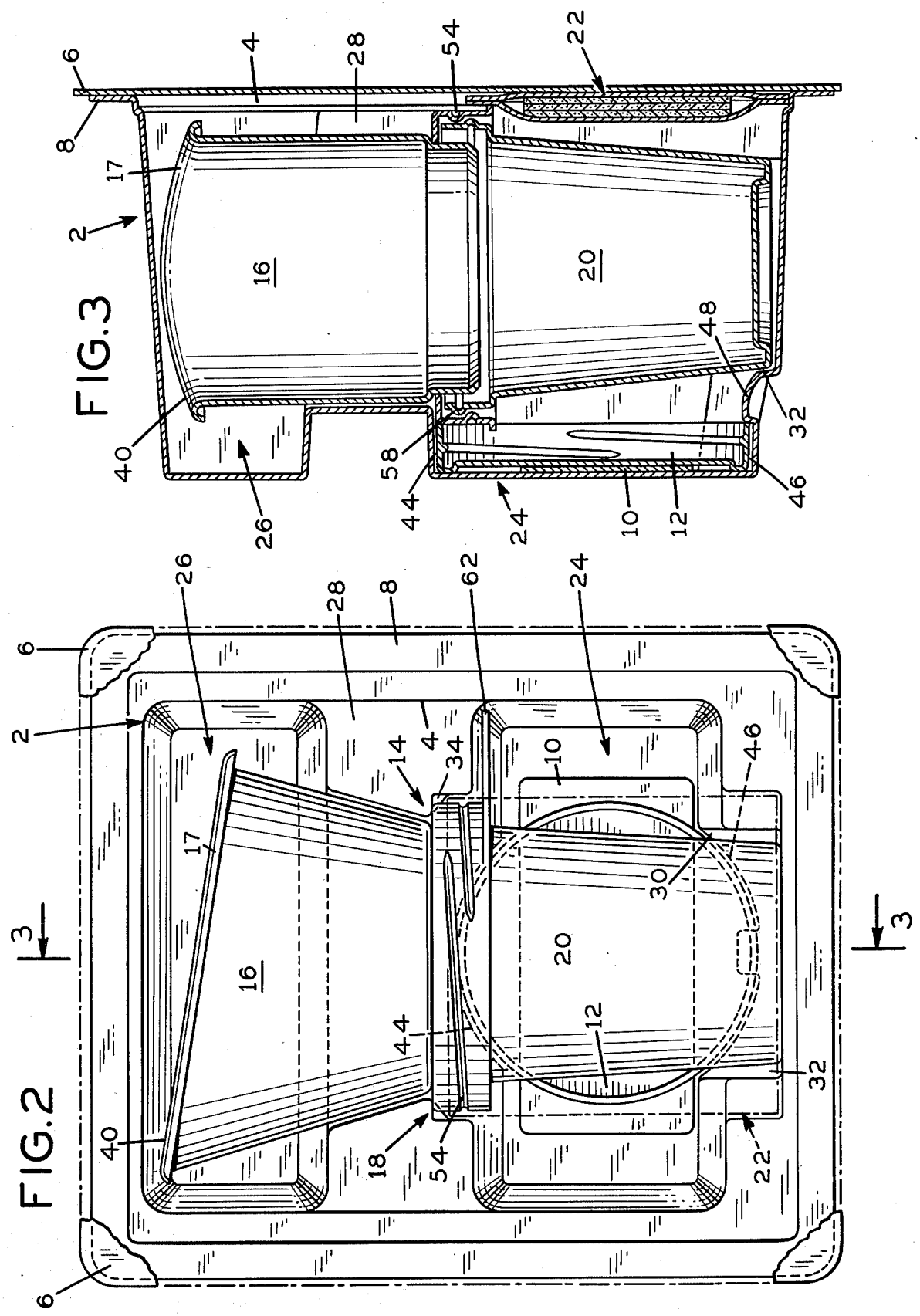

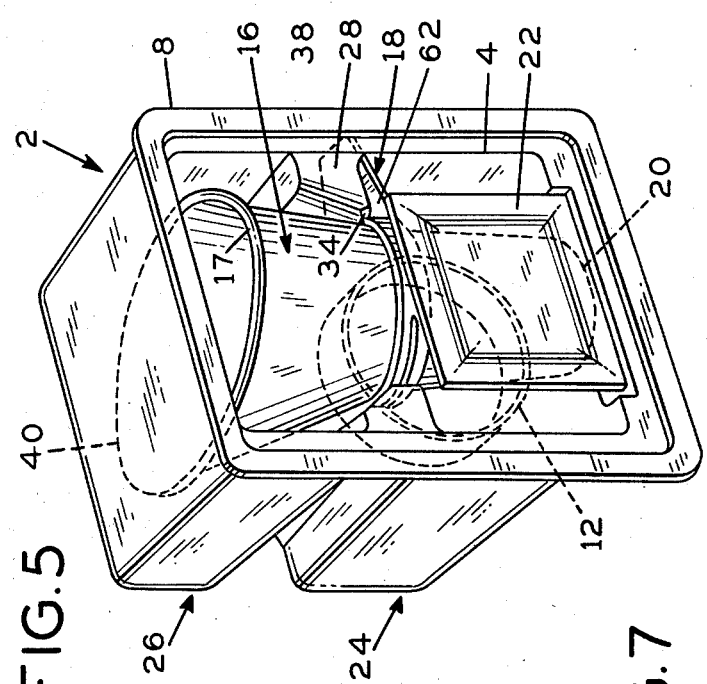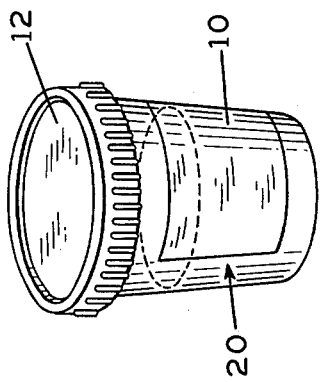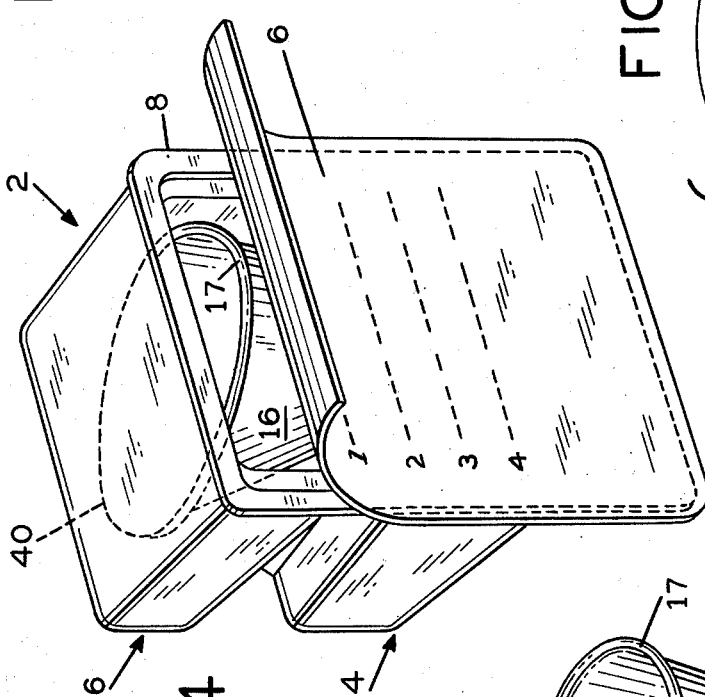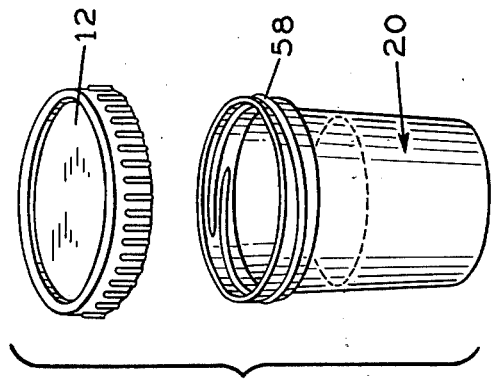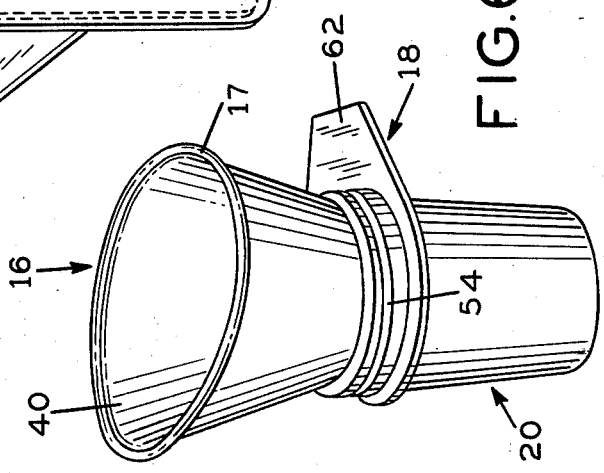

MID-STREAM URINE COLLECTION DEVICE AND PACKAGE THEREFOR

BACKGROUND OF THE INVENTION

This invention relates to a mid-stream urine collection device and more particularly to a system, package and device for urine collection which is sanitary and efficient and wherein the parts are packaged in a sterile environment in such a way that they are removed in the order of their use which helps prevent contamination.

Taking urine samples for the purpose of testing the urine for presence of infection or levels of bacteria indicating various diseases and health defects is a common practice. Frequently, this is done by having the patient urinate into a glass or other container for subsequent testing and analysis. One of the problems with this and other urine sampling techniques is that the initial urine surge may indicate the presence of bacteria which would not be present after the initial urine surge. Another problem with prior art urine testing systems is that the components used in the urine collection become contaminated either prior or during use, thus resulting in inaccurate or misleading test results.

OBJECTS

With the foregoing in mind, it is an object of this invention to provide a new and improved urine sampling package and system which is adapted to collect and maintain urine samples under aseptic conditions.

Another object of this invention is to provide a urine sampling device adapted for use by males and females wherein the components are packaged under sterile conditions and are removed in their order of use to prevent contamination.

Another object of this invention is to provide a urine sampling system useable by males and females which permits urine sampling, after the initial urine surge, in a manner which maximizes obtaining urine samples free from outside contamination.

Another object of this invention is to provide a sterile package having therein the components necessary to obtain a urine sample wherein the components are maintained within the package in a sterile condition and the components are removed in their order of use.

Another object of this invention is to provide a self-contained package having the necessary components for taking a urine sample including cleansing means, a container, funnel assembly, cap means for the container and label means, all packaged in a sterile condition and positioned within the package so that they are removed in their order of use and are removed aseptically.

Additional objects and advantages of the invention will be set forth in the description which follows and in part will be obvious from the description. The objects and advantages of this invention being realized and obtained by means of the instrumentation, parts, apparatus and assemblage being particularly pointed out in the appended claims.

The invention consists of the instrumentation, parts, steps, construction and improvements shown and described.

BRIEF DESCRIPTION OF THE INVENTION

Briefly described, the invention includes a container for packaging the components of the urine collection system. The package is constructed so that one entire side can be removed. The outside surface and the inside surface of the removable side contains instructions concerning the manner and order of use of the components, including instructions to be followed before the package is opened.

The inside surface of the removable side contains the same operating instructions except that the instructions to be followed prior to use can be omitted if desired.

After the package has been opened there is presented to the user a packaged cleaning means with instructions on how to use the cleaning means to cleanse and prepare the genital area prior to taking a urine sample. The next item to be removed from the package is a funnel-container assembly unit which permits a urine sample to be tken without the user's hands contaminating the sample.

Thereafter, the funnel-container assembly unit is disassembled and a cap aseptically removed from the package so that the cap can be attached to the container thereby isolating the urine sample. Subsequently, a label is removed from the package and such pertinent information as necessary recorded thereon so that the label when placed on the urine sample container will indicate the necessary information.

The system or method of operation is such that it is extremely unlikely that the urine sample will become contaminated prior to, during, or after the sampling procedure.

The accompanying drawings which are incorporated in and constitute a part of this specification, illustrate an embodiment of the invention and together with the description serve to explain the principles of the invention.

OF THE DRAWINGS

FIG. 1 is an exploded view showing the various components before assembly into a package.

FIG. 2 is a vertical view of the package with the protective cover partly broken away to show the various components in packaged juxtaposition.

FIG. 3 is a vertical section taken along line 3—3 of FIG. 2.

FIG. 4 is a perspective showing of the package with the cover partly removed.

FIG. 5 shows the cover completely removed.

FIG. 6 shows the container assembly before use.

FIG. 7 shows the container and cover in exploded relationship after use.

FIG. 8 shows the container with cover attached and the identification label affixed.

DETAILED DESCRIPTION OF INVENTION

Referring to FIG. 1 the components of the invention are shown prior to their assembly within the package to form a urine sample collection system.

The packaging means consists of a molded plastic base 2 preferably made of styrene or the like which is transparent to permit viewing of the contents. As will be explained subsequently the base member 2 is shaped and constructed so as to neatly package the urine collection components.

The open side 4 of the base through which the urine sample collection components are inserted and removed is adapted to be closed, after the components have been assembled within the base, by a cover 6. The outer periphery 8 of the base 4 and the outer periphery of the cover 6 are held together in some convenient manner such as an adhesive or by heat sealing in such a manner that the cover 6 can be peeled from the base 4 to permit access to the urine sampling collection components. The components are placed within the base 4 in the reverse order of their use and then sterilized.

Thus, label 10 is first followed by screw cover 12 and then the funnel-container assembly 14 consisting of funnel 16, tab member 18 and container 20. The last item placed in the base 4 is the first one to be removed and that is the cleansing member 22.

The base or package member which is preferably made of molded synthetic plastic such as styrene consists of two major cavities, lower cavity 24 and upper cavity 26 with an inwardly extending divider 28.

The bottom wall has a curvilinear recess 30 including a semi-circular portion 32 which conforms to the shape of the container 20. The curvilinear recess has a height sufficient to stabilize the container. The bottom surface of the divider 28 has a curvilinear cut-away portion 34 which generally conforms to the curvature of the circular portion 36 of the tab member 18.

The vertical wall 38 of the divider 28 above the cut-away or recessed portion 34 has a tapered surface to accommodate the increasing diameter of the funnel 16 and the open end 40 of the funnel 16 is accommodated by the upper cavity 26. The rear wall 42 of the lower cavity 24 is substantially flat and includes upper 44 and lower 46 arcuate portions shaped and spaced to accommodate the diameter of the screw cap 12. The lower arcuate surface 46 has an abutment 48 spaced from the rear wall 42 a distance approximately equal to the height of the screw cap 12 so as to wedge the same into position within the base 4. The screw cap is positioned within the package so that the outside of the cap only is touched by the fingers when it is removed from the package.

The flat surface of rear wall 42 is of sufficient size to accommodate the label 10.

The base member 4 is thus shaped and constructed to show that all the urine sample components can be placed within the base 4, in a sterile condition or sterilized after being so positioned and the cover 6 placed into position so that there is a neat sterilized assemblage of components.

As previously indicated, an object of this invention is to maintain the component parts in a sterile condition during the urine sampling procedure.

With the urine collection system in the condition of FIG. 2, the user reads the instructions set forth in the outside surface of the cover. These instructions include instructions as to what to do prior to use of the packaged components. For example:

"1. Wash hands."

"2. Peel back cover from corner (instructions are also on inside flap)."

Thus, the use instructions are presented on the inside surfaces of the cover 4. For convenience and to avoid confusion, the instruction on the inside of cover 4 may not be repeated since the steps, above quoted, have already been accomplished.

After the cover 4 has been removed the last component placed within the base will be the first component to be removed and is a packet of towelettes 22. The towelettes are commercially available and can consist of small paper towels, e.g., three which have been soaked in a cleansing means such as benzalkonium chloride, idophor or Castille soap. Instead of providing a single package with, for example, three towelettes, it is also contemplated that separate individually packaged towelettes can be provided. The packet of towelettes 22 on each side contains instructions for using the towelettes. Thus, one side of the packet contains instructions for using the towelettes to cleanse the urinary area of a female and the other side of the packet contains instructions for cleansing the urinary area of a male, or a separate sheet for cleansing procedure may be provided.

Following the cleansing step, the funnel-container assembly is removed from its packaged position within the base 4.

The funnel member 16 includes a downwardly extending flange 50 having a circumferential recess 52. The funnel-container assembly further includes a tab member 18. The tab member 18 includes interior threads 54 adapted to be placed in threaded engagement with the exterior threads 58 in the top of the container 20. The tab member 18 further includes a radially inwardly extending flange 60 adapted to have a snap-fit engagement with recess 52 on the funnel member 16. The funnel member 16 and tab member 18 can be separate members which are removably connected. There are instances, for example, where a sample is being taken from a male where the funnel is unnecessary.

The funnel member is made of a flexible soft plastic material such as styrene which resists crushing when placed between the user's legs and is anatomically shaped. The upper rim 17 of the funnel is rolled outward and downward so that there is no sharp edge contacting the user. In addition, the upper rim 17 is somewhat slanted (see FIG. 2) so that when the device is used by a female it can be placed in the appropriate position with a minimum amount of movement by the user. In other words the device can be used by a female patient while in the prone position without disturbing the position of the patient.

It will be understood that as assembled within the base 4 the funnel assembly components are in their attached condition shown in FIG. 6.

After the removal of the funnel-container assembly 14 from the base 4, the user urinates, briefly, into the toilet and then briefly into the funnel-container assembly. The first gush of urine is directed to the toilet since it would contain bacteria, etc., not found in later stages of the urine flow. After a sufficient urine sample has been obtained urine can then be redirected to the toilet.

It will be appreciated that the funnel-container assembly will be held by the gripper portion 62 of the tab member 18 during the removal and sample taking process to avoid contamination of the urine sample.

After the urine sample has been taken, the funnel-container assembly is placed on a flat surface and the tab member 18 and funnel member 16 are separated from the container by turning or twisting the tab member with respect to the container 20. The funnel and tab assembly are then thrown away.

At this point the screw cover 20 is removed from the base 4 and attached to the container 20 (see FIG. 7). The gum label 10 is then removed from the base, filled in with the appropriate information and attached to the container 20 (FIG. 8).

What is claimed is:

1. A urine sample collection system comprising:
   (a) a supply of cleansing towelettes;
   (b) a funnel-container assembly including a funnel and a container and a tab member removably connecting said funnel and said container;
   (c) a cap member adapted to be secured to the container after collection of the urine sample;

(d) a label member adapted to contain identifying information adapted to be secured to the container; and
(e) packaging means including a base member and a cover for packing said components of paragraphs (a)–(d) in a sterile condition and so that said components can be aseptically removed in their order of use, said packaging means includes a base member hollowed out to receive the urine collection components, the open side of said base member being closed by a side which is removable when the system is ready for use, said removable side maintaining the urine collection components in sterile condition while the components are in packaged condition, said base member includes an upper and a lower cavity; an inwardly extending wall between said upper and lower cavities forming a divider tapered upwardly to accommodate the shape of said funnel member; a curvilinear recess formed in the bottom wall of said lower cavity, said curvilinear recess including a semi-circular portion; said lower cavity having a rear wall which is substantially flat, said rear wall including inwardly extending curved portions spaced apart a distance equal to the diameter of said cup;
(f) at least one surface of said removable side contains use instructions;
(g) said label being placed in contact with said flat surface of said rear wall;
(h) said cap member being placed between said inwardly extending curved portions of said rear wall;
(i) said funnel-container assembly being positioned with the container in engagement with said curvilinear recess in the bottom wall of said lower cavity and said funnel extending into said upper cavity; and
(j) a supply of towelettes placed within said base.

* * * * *